United States Patent [19]
Britton

[11] Patent Number: 5,618,951
[45] Date of Patent: Apr. 8, 1997

[54] PROCESS FOR PREPARING 2,2-DIFLUOROKETENE SILYL ACETALS AND α, α-DIFLUORO-βSILYLOXY-1, 3-DIOXOLANE-4-PROPANOIC ACID ESTERS

[75] Inventor: Thomas C. Britton, Carmel, Ind.

[73] Assignee: Eli Lilly and Company, Indianapolis, Ind.

[21] Appl. No.: 451,284

[22] Filed: May 26, 1995

Related U.S. Application Data

[63] Continuation-in-part of Ser. No. 307,122, Sep. 16, 1994, abandoned, which is a continuation-in-part of Ser. No. 160,549, Nov. 30, 1993, abandoned.

[51] Int. Cl.$^6$ ........................................................ C07F 7/18
[52] U.S. Cl. .............................................. 549/214; 556/446
[58] Field of Search .............................. 549/214; 556/446

[56] References Cited

U.S. PATENT DOCUMENTS

| | | |
|---|---|---|
| 4,414,372 | 11/1983 | Farnham et al. . |
| 4,417,034 | 11/1983 | Webster . |
| 4,482,729 | 11/1984 | Ishikawa et al. . |
| 4,508,880 | 4/1985 | Webster . |
| 4,746,750 | 5/1988 | Revis . |
| 4,754,046 | 6/1988 | Revis . |
| 4,824,980 | 4/1989 | Schulz, Jr. et al. . |
| 4,824,981 | 4/1989 | Schulz, Jr. et al. . |
| 5,041,587 | 8/1991 | Itoh et al. . |

FOREIGN PATENT DOCUMENTS

| | | |
|---|---|---|
| 0184692 | 6/1986 | European Pat. Off. . |
| 2067250 | 3/1990 | Japan . |
| 2270841 | 11/1990 | Japan . |

OTHER PUBLICATIONS

Ainsworth, C., et al., *J. Organometallic Chem.*, 46 (1972), pp. 59–71.
Kita, Y., et al., *Tetrahedron Letters*, 24:12 (1983), pp. 1273–1276.
Brown, C., *J. Org. Chem.*, 39:9 (1974), pp. 1324–1325.
Kuo, Y., et al., *Chemical Communications*, (1971), pp. 136–137.
Petrov, A., et al., *J. Gen. Chem.*, (U.S.S.R.), 29 (1959), pp. 2896–2899.
Ojima, I., et al., *J. Organometallic Chem.*, 111 (1976), pp. 43–60.
Howe, J., et al., *J. Organometallic Chem.*, 208 (1981), pp. 401–406.
Yoshii, E., et al., *Chem. Pharm. Bull.*, 22:11 (1974), pp. 2767–2769.
Ainsworth, C., and Chen, F., *J. Am. Chem. Soc.*, 94:11 (1972), pp. 4037–4038.
Kitagawa, O., et al., *Tetrahedron Letters*, 29:15 (1988), pp. 1803–1806.
Burton, D., and Eason, J., *J. of Fluorine Chemistry*, 38 (1988), pp. 125–129.
Kuroboshi, M., and Ishihara, T., *The Chemical Society of Japan*, 63 (1990), pp. 428–437.
Taguchi, T., et al., *Tetrahedron Letters*, 29:41 (1988), pp. 5291–5294.
Takeuchi, Y., et al., *J. Chem. Soc. Perkin Trans. I*, (1988), pp. 1149–1153.
Greuter, H., et al., *Tetrahedron Letters*, 29:27 (1988), pp. 3291–3294.
Yamana, M., et al., *Tetrahedron Letters*, 24:5 (1983), pp. 507–510.
Easdon, J., New Synthetic Methodology for Organofluorine Compounds, Thesis Jul. 1987, University of Iowa, pp. 162–206 and pp. 267–278.
Lang, R., and Schaub, B., *Tetrahedron Letters*, 29:24 (1988), pp. 2943–2946.
Mcharek, S., et al., *J. of Organometallic Chem.*, 401 (1991) pp. 211–215.
Lang, R., *Helvetica Chimica Acta*, 71 (1988), pp. 369–373.
Kitagawa, O., et al., *Chemistry Letters (Japan)*, (1990), pp. 1307–1310.

*Primary Examiner*—Nicky Chan
*Attorney, Agent, or Firm*—Margaret M. Brumm; David E. Boone

[57] ABSTRACT

A process for preparing 2,2-difluoroketene silyl acetals and α,α-difluoro-β-silyloxy-1,3-dioxolane-4-propanoic acid esters using these acetals.

13 Claims, No Drawings

PROCESS FOR PREPARING 2,2-DIFLUOROKETENE SILYL ACETALS AND α,α-DIFLUORO-βSILYLOXY-1, 3-DIOXOLANE-4-PROPANOIC ACID ESTERS

This application is a continuation-in-part of application Ser. No. 08/307,122, filed Sep. 16, 1994, now abandoned, which is a continuation-in-part of application Ser. No. 08/160,549, filed Nov. 30, 1993, now abandoned.

BACKGROUND OF THE INVENTION

1. Field of the Invention

The invention pertains to the field of pharmaceutical chemistry and provides a process for preparing 2,2-difluoroketene silyl acetals useful as pharmaceutical intermediates and a process for employing these acetals in the preparation of α,α-difluoro-β-silyloxy-1,3-dioxolane-4-propanoic acid ester intermediates.

2. State of the Art

Ketene silyl acetals were first prepared by Petrov, et al.; see *J. Gen. Chem. (USSR)*, 29, 2896–99 (1959). H. Greuter, et al., *Tetrahedron Lett.*, 29 (27), 3291–94 (1988) teach the use of allylic esters of chlorodifluoroacetic acid in silicon induced Reformatsky-Claisen reactions in which 2,2-difluoroketene silyl acetals are the inferred intermediates. M. Yamana, et al., *Tetrahedron Lett.*, 24 (5), 507–10 (1983) and Y. Takeuchi, et al., *J. Chem. Soc. Perkin Trans.* I, 1149–53 (1988) teach the preparation of difluoro silyl enol ethers on reaction of chlorodifluoromethyl ketones with zinc dust and trimethylsilyl chloride.

2,2-Difluoroketene silyl acetals have been prepared from the direct reaction of bromodifluoroacetate esters, zinc amalgam and chlorotrimethyl silane in triglyme; see J. C. Easdon, *New Synthetic Methodology for Organofluorine Compounds*, Ph.D. Thesis, Chemistry Department, Graduate College of the University of Iowa, July 1987. Kobayashi, et al. in Japanese Patent 2,067,250 and *Tetrahedron Lett.*, 29 (15), 1803–06 (1988) describe the preparation of 2,2-difluoroketene silyl acetals by reacting methyl iododifluoroacetate with zinc dust in acetonitrile and treating the resultant organozinc species (Reformatsky reagent) with trialkylsilyl chloride. They further disclose the preparation of α,α-difluoro-2,2-dimethyl-β-[(trialkylsilyl)oxy]-1,3-dioxolane-4-propanoic acid methyl esters from the reaction of 2,3-O-isopropylidene-D-glyceraldehyde with the in situ-generated difluoroketene silyl acetals. The 2,2-difluoroketene silyl acetals proved to be superior to the corresponding Reformatsky reagents in that they afforded much higher erythro/threo (anti/syn) ratios in the condensation reaction with 2,3-O-isopropylidene glyceraldehyde than the latter reagents.

Matsumura, et al., in Japanese Patent 2,270,841, described the preparation of anti-α,α-difluoro-2,2-dimethyl-β-[(trialkylsilyl)oxy]-1,3-dioxolane-4-propanoic acid esters from the reaction of bromodifluoroacetate and iododifluoroacetate esters with trialkylsilyl chloride and zinc in acetonitrile, followed by treatment with 2,3-O-isopropylidene-D-glyceraldehyde and titanocene dichloride.

Esters of chlorodifluoroacetic acid are reported by R. W. Lang and B. Schaub, *Tetrahedron Lett.*, 24, 2943–6 (1988) to undergo Reformatsky-type condensation reactions with aldehydes on treatment with activated zinc dust in dimethylformamide. However, low yields were obtained when they attempted to condense aliphatic, enolizable aldehydes with chlorodifluoro-acetate under these conditions, unless ultrasonication was used. S. Mcharek, et al., *J. Organometallic Chem.*, 401, 211–15 (1991) similarly report Reformatsky-type condensation reactions of methyl chlorodifluoroacetate and simple aliphatic aldehydes in dimethylformamide, or mixtures of methylene chloride and dimethylformamide, by electrolytic reduction at a sacrificial zinc anode in the presence of a nickel catalyst. Note that the reaction of ethyl chlorodifluoroacetate with zinc dust and trialkylsilyl chloride in dimethylformamide does not afford the corresponding 2,2-difluoroketene silyl acetal, but rather yields the O-silylated carbinol amine formally derived from its condensation with the solvent; see R. W. Lang, *Helv. Chim. Acta.*, 71, 369–73 (1988).

In addition to the utility described above, 2,2-difluoroketene acetals have proven useful as intermediates for preparing 3-amino-2,2-difluoro esters as described by T. Taguchi, et al., *Tetrahedron Lett.*, 29, 5291–4 (1988). Similarly, Kitagawa, et al., *Chem. Lett.*, 1307–10 (1990), have reported that 2,2-difluoroketene silyl acetals readily undergo Michael condensation with α,β-unsaturated carbonyl compounds or their derived acetals. These adducts have proven useful in the preparation of difluoro derivatives of the α-amino acids, glutamic acid and lysine. The α,α-difluoro-2,2-dimethyl-β-[(trialkylsilyl)oxy]-1,3-dioxolane-4-propanoic acid esters themselves are useful as intermediates in the preparation of antitumor and antiviral nucleosides.

An object of the present invention is to provide a process for preparing 2,2-difluoroketene silyl acetals from esters of chlorodifluoroacetate.

Another object of the invention is to provide a process for preparing α,α-difluoro-β-silyloxy-1,3-dioxolane-4-propanoic acid esters using the 2,2-difluoroketene silyl acetals generated in situ.

Other objects and advantages of the invention will become apparent from the following description of embodiments.

SUMMARY OF THE INVENTION

This invention provides a process for preparing 2,2-difluoroketene silyl acetals of the formula

wherein $R^1$, $R^2$, $R^3$, and $R^4$ are each independently selected from alkyl and aryl groups or substituted alkyl or substituted aryl groups; comprising contacting a chlorodifluoroacetate of the formula

wherein $R^4$ is as defined above; with a halosilane of the formula

wherein X is chloro or bromo, and $R^1$, $R^2$, and $R^3$ are as defined above; in a solvent selected from the group consisting of cyclic and acyclic tetraalkyl ureas, mixtures thereof, or a mixture consisting of the solvent and a co-solvent which is selected from the group consisting of acetonitrile, tetrahydrofuran and 1,2-dimethoxyethane or mixtures thereof; in the presence of a reducing agent.

Another aspect of this invention provides a process for preparing α,α-difluoro-β-silyloxy-1,3-dioxolane-4-propanoic acid esters of the formula

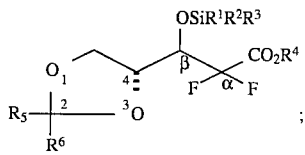 (IV)

wherein $R^1$ thru $R^4$ are as defined above; $R^5$ and $R^6$ are independently selected from hydrogen and $C_1$–$C_3$ alkyl or together form part of a carbocyclic ring in which they comprise a —$(CH_2)_n$— moiety where n is an integer from 3 to 6; in which a reaction mixture containing the 2,2-difluoroketene silyl acetal (I), prepared as described above, is treated with a glyceraldehyde derivative of the formula

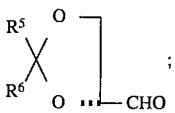 (V)

wherein $R^5$ and $R^6$ are defined as above.

DESCRIPTION OF THE INVENTION

Throughout this document, all temperatures are in degrees Celsius, all proportions, percentages and the like are in weight units and all mixtures are in volume units, except where otherwise indicated. The term "alkyl" alone or in combination refers to straight or branched or cyclic chain aliphatic hydrocarbon groups which contain up to 7 carbon atoms such as methyl, ethyl, n-propyl, isopropyl, n-butyl, isobutyl, cyclopentyl, cyclohexyl, t-butyl, n-pentyl, n-hexyl, and 3-methylpentyl groups. The alkyl group can also have an aryl substituent, for example, benzyl is meant to be included. Alkyl groups preferably contain up to 4 carbon atoms. The term "aryl" alone or in combination refers to aromatic carbocyclic groups including phenyl, naphthyl, and substituted derivatives thereof. The term "substituted" alone or in combination, as applied to either alkyl or aryl, refers to substitution by at least one or more of the groups selected from cyano, halo, nitro, alkoxy, alkyl and aryl.

The methyl and ethyl esters of formula (II) are commercially available. The esters of formula (II) may be prepared by treating chlorodifluoroacetyl chloride with an equimolar amount of an alcohol having the general formula $R^4OH$ in an inert solvent, such as methylene chloride, in the presence of a slight excess (1.1 to 1.5 molar equivalents) of a tertiary amine base, such as triethylamine, at −78° to 25° C. The esterification may optionally be conducted in the presence of an acyl transfer catalyst such as 4-dimethylaminopyridine. The crude ester product is then washed successively with 0.5N aqueous $NaHSO_4$, and 1N pH 7 phosphate buffer, dried over $MgSO_4$, and isolated in purified form by fractional distillation. Examples of esters (II) prepared by this procedure include: isobutyl chlorodifluoroacetate; isopropyl chlorodifluoroacetate; and t-butyl chlorodifluoroacetate.

Halosilanes (III) suitable for use in the present process are commercially available. An extensive compilation of halosilane compounds is described in the *Petrarch Systems Silanes & Silicones, Register and Review*, Petrarch Systems, 1987. Halosilanes are generally employed to introduce silyl protecting groups into organic compounds. They are also discussed by T. W. Greene and P. G. M. Wuts, in *Protecting Groups in Organic Synthesis*, 2nd Ed., J. Wiley and Sons, Inc. New York (1991). Preferred halosilanes are selected from the group consisting of chloro- or bromo- -trimethylsilane, -triethylsilane, -isopropyldimethylsilane, -t-butyldimethylsilane, -(triphenylmethyl)dimethylsilane, -t-butyldiphenylsilane, -methyldiisopropylsilane, -methyldi-t-butylsilane, -tribenzylsilane, -tri-p-xylylsilane, -triisopropylsilane, and -triphenylsilane.

Solvents suitable for use in the present process are cyclic- and acyclic-tetraalkyl ureas. Preferred solvents include 1,3,4,5-tetramethyl-2-imidazolidinone; 1,3,4,4-tetramethyl-2-imidazolidinone; 1,3,4,4,5,5-hexamethylimidazolidinone; 1,3,4,6-tetramethyl-3,4,5,6-tetrahydro-2(1H)-pyrimidinone; 1,3,4-trimethyl-3,4,5,6 -tetrahydro-2(1H)-pyrimidinone; 1,3,5-trimethyl-3,4,5,6-tetrahydro-2(1H)-pyrimidinone; 1,3-diisopropyl-1,3-dimethyl urea; 3-ethyl1,3-dimethyl-1-isopropyl urea; 1,3,5,5-tetramethyl-3,4,5,6-tetrahydro-2(1H)-pyrimidinone; 1,3-dimethyl-3,4,5,6-tetrahydro-2(1H)-pyrimidinone (DMPU); 1,3-dimethyl-2-imidazolidinone (DMI); 1,1,3,3-tetramethyl urea (TMU); 1,1,3,3-tetraethyl urea; 1,1,3-triethyl-3-methyl urea; 1,3,4, 4-tetramethyl-tetrahydro-pyrimidin-2-one; 1-ethyl-1,3,3-trimethyl urea; 1-isopropyl-1,3,3-trimethyl urea; hexahydro-1, 3-dimethyl-2H-1,3-diazepin-2-one; 1-ethyl-3-methyl-imidazolidin-2-one; 1-tert-butyl-1,3,3-trimethyl urea; 1,3-diethyl-1,3-dimethyl urea; di-(pyrrolidin-1-yl)-methanone; 1,3-diethyl-imidazolidin-2-one; 1,3,4-trimethyl-imidazolidin-2-one; 1,1-diethyl-3,3-dimethyl urea; 1,3-diethyl-3,4,5, 6-tetrahydro-pyrimidin-2-one; and 1,3,4,4,5-pentamethyl-2-imidazolidinone and mixtures thereof. More preferred solvents are DMPU, DMI and TMU. The most preferred solvent is DMI. Other suitable cyclic- and acyclic-tetraalkyl urea solvents would be apparent to those skilled in the art.

It is also possible, though not preferred, to use mixtures of the above cyclic- and acyclic-tetraalkyl ureas with co-solvents. The co-solvents are selected from the group consisting of acetonitrile, tetrahydrofuran and, 1,2-dimethoxyethane, or mixtures thereof. It is preferred to not use a co-solvent because use of a co-solvent generally leads to a reduction in process yield.

Reducing agents suitable for use in the present process are described by A. Furstner, *Synthesis*, 571 (1989) and include zinc, magnesium, zinc/copper couple, zinc/silver couple, cadmium, nickel, indium, cerium, and lithium. Metal salts having a favorable reduction potential may also be used and are selected from chromium(II) chloride, samarium(II) iodide and titanium(II) chloride. Also, cerium(III) halides, disodium telluride or combinations of trialkylantimony/iodine or tributyl(phenyl)stannyllithium and diethylaluminum chloride may be used. However, because of its low cost and ready availability the preferred reducing agent is zinc. Although the zinc reducing agent employed may optionally be a highly activated form with enhanced reactivity as described by Erdik, in *Tetrahedron*, 43 (10), 2203–12 (1987), it is not necessary to use an activated form of zinc in this process. In fact, it is most convenient and economical to employ commercially available zinc dust without any prior activation.

It will be recognized by one of ordinary skill in the art that the optimal conditions for forming (I) by this process will be dramatically influenced by the reducing agent employed, and its activity. Additional factors that will influence the optimal conditions are the specific halosilane (III), chlorodifluoro ester (II) and solvent that is employed. For example, it has been observed that when the process is conducted with commercial zinc dust without any prior activation, chlorotrimethylsilane and methyl chlorodifluoroacetate in 1,3-dimethylimidazolidin-2-one, the reaction is conveniently carried out from about 0° C. to about 50° C. The yield of the ketene silyl acetal formed can conveniently be monitored as the reaction proceeds by $^{19}$F NMR integration versus a $C_6F_6$ internal standard. In studying the reaction in this manner, it has been observed that the yield of (I) typically reaches a maximum value over time then decreases slowly with time as it is converted to the corresponding isomeric α-silyldifluoroacetate ester. We have determined that this α-silyldifluoroacetate ester, which forms as a degradation product of (I), does not react with aldehyde (V) under these conditions. Therefore, in order to achieve maximal conversion of the chlorodifluoro ester (II) to (IV), it is important to introduce aldehyde (V) prior to or at the time the yield of the difluoroketene silyl acetal (I) is at a maximum.

When prepared as described above, (I) may be reacted in situ with aldehyde (V) to form α,α-difluoro-β-silyloxy-1,3-dioxolane-4-propanoic acid ester (IV). This reaction sequence constitutes a one pot process for the preparation of (IV). The present process has the advantage of being economical since it employs inexpensive and readily available (II). The process also provides higher yields of erythro-(IV) and significantly higher erythro (anti) selectivity than the corresponding reaction of (V) with the Reformatsky reagent derived from (II).

The condensation of aldehyde (V) with the in situ-generated (I) does not require the introduction of additional Lewis acids. Zinc chloride ($ZnCl_2$) is the by-product of the ketene silyl acetal-forming reaction when Zn(0) is used as the reducing agent. It is presumed that the $ZnCl_2$, or the complex it forms with the urea solvent, serves as an effective catalyst in the condensation reaction of (I) with (V).

Aldehydes (V) suitable for use in the present process are generally known in the art. Methods for preparing such compounds are discussed by Jurczak, et al. in *Tetrahedron*, 42, 447–488 (1986) and Schmid and Bradley in *Synthesis*, 1992, 587–590. O-Protected glyceraldehyde derivatives such as 2,3-O-alkylidene glyceraldehydes, are particularly useful in this process. Especially preferred 2,3-O-alkylidene glyceraldehydes are those in which the alkylidene protecting group is 2-propylidene, 3-pentylidene, cyclopentylidene, or cyclohexylidene.

The preferred temperature for the reaction of in situ-generated (I) with aldehyde (V) to form the α,α-difluoro-β-silyloxy-1,3-dioxolane-4-propanoic acid esters (IV) ranges from about −10° C. to about 70° C. when Zn(0) is employed as the reducing agent. It will be generally recognized by one of ordinary skill in the art that the preferred conditions for the reaction will be influenced by the nature of the solvent, the reducing agent, and the specific structures of (I) and aldehyde (V).

The following examples illustrate specific aspects of the present invention and are not intended to limit the scope thereof in any respect and should not be so construed.

EXAMPLE 1

Methyl trimethylsilyl 2,2-difluoroketene acetal

To a mixture of 2.9 g (44 mg-atom, 1.2 eq) of zinc dust and 15 mL of 1,3-dimethylimidazolidin-2-one, stirred at 24° C. under dry nitrogen, was added 6.2 mL (5.3 g, 48 mmol, 1.2 eq) of chlorotrimethylsilane. The mixture was stirred at 25° C. for 45 minutes, and then cooled to 0°–5° C. Hexafluorobenzene (1.00 mL), a reaction calibration standard, and methyl chlorodifluoroacetate (4.40 mL, 5.87 g, 40.6 mmol, 1.0 eq) were added, the cooling bath was removed, and the mixture was allowed to exotherm to 32° C. over a 45 minute period. After an additional 30 minutes, the exotherm having subsided, the mixture was heated to 40°–42° C. At various times (after heating), reaction aliquots (0.7 mL) were withdrawn via syringe, filtered through a 0.45µ Teflon (Teflon is a registered Trademark of E.I. DuPont DeNemours & Company, Wilmington, Del., U.S.A.) syringe filter under dry nitrogen, diluted with an equal volume of $C_6D_6$ and assayed by 282 MHz $^{19}$F NMR (Nuclear Magnetic Resonance) spectroscopy. Yields were determined by integration of the $^{19}$F NMR signals of the 2,2-difluoro ketene silyl acetal product (AB quartet, $J_{FF}$=107.7, centered at 85.6 ppm downfield from $C_6F_6$) as compared to the $C_6F_6$ internal standard:

| Aliquot | Elapsed Time (Hrs.) | % Yield |
| --- | --- | --- |
| 1 | 1.5 | 37 |
| 2 | 3.0 | 43 |
| 3 | 5.0 | 46 |
| 4 | 7.0 | 47 |
| 5 | 17.0 | 43 |

EXAMPLE 2

Methyl trimethylsilyl 2,2-difluoroketene acetal

To a mixture of 3.0 g (46 mg-atom, 1.1 eq) of zinc dust and 15 mL of 1,3-dimethylimidazolidin-2-one, stirred at 23° C. under dry nitrogen, was added 6.2 mL (5.3 g, 48 mmol, 1.2 eq) of chlorotrimethylsilane. The mixture was stirred at room temperature for 45 minutes then cooled to 5° C. Hexafluorobenzene (0.5 mL), a reaction calibration standard, and methyl chlorodifluoroacetate (5.86 g, 40.6 mmol, 1.0 eq) were added. The cooling bath was removed and the reaction was allowed to exotherm to a maximum temperature of 43° C. over a 50 minute period. After an additional 20 minutes, the reaction was heated 40° C. for 130 minutes. A reaction aliquot, withdrawn and assayed by $^{19}$F NMR spectroscopy as described above, afforded a 46% yield of the title compound.

EXAMPLE 3

Ethyl trimethylsilyl 2,2-difluoroketene acetal

To a mixture of 1.46 g (22.3 mg-atom, 1.1 eq) of zinc dust and 7.5 mL of 1,3-dimethylimidazolidin-2-one, stirred at 23° C. under dry nitrogen, was added 3.1 mL (2.7 g, 24 mmol, 1.2 eq) of chlorotrimethylsilane. The mixture was stirred at room temperature for 50 minutes and cooled to 5° C. Hexafluorobenzene (0.25 mL), a reaction calibration standard, and ethyl chlorodifluoroacetate (3.26 g, 20.6 mmol, 1.0 eq) were added. The cooling bath was removed and the reaction was allowed to exotherm to a maximum temperature of 28° C. over a 2 hour period. The mixture was heated to 40° C. for 3.5 hours and 50° C. for 1 hour additional. A reaction aliquot, withdrawn and assayed by $^{19}$F NMR spectroscopy as described above, afforded a 44% yield of the title compound.

EXAMPLE 4

Isopropyl trimethylsilyl 2,2-difluoroketene acetal

To a mixture of 1.46 g (22.3 mg-atom, 1.1 eq) of zinc dust and 7.5 mL of 1,3-dimethylimidazolidin-2-one, stirred at 23° C. under dry nitrogen, was added 3.1 mL (2.7 g, 24 mmol, 1.2 eq) of chlorotrimethylsilane. The mixture was stirred at room temperature for 30 minutes. Hexafluorobenzene (0.25 mL) was added and the mixture was heated to 40° C. Isopropyl chlorodifluoroacetate (3.53 g, 20.5 mmol, 1.0 eq) was added over a 30 minute period and the mixture was heated to 40° C. for 15 hours. A reaction aliquot, withdrawn and assayed by $^{19}$F NMR spectroscopy as described above, afforded a 54% yield of the title compound.

EXAMPLE 5 t-Butyl trimethylsilyl 2,2-difluoroketene acetal

To a mixture of 1.54 g (23.5 mg-atom, 1.1 eq) of zinc dust and 7.5 mL of 1,3-dimethylimidazolidin-2-one, stirred at 23° C. under dry nitrogen, was added 3.1 mL (2.7 g, 24 mmol, 1.2 eq) of chlorotrimethylsilane. The mixture was stirred at room temperature for 45 minutes. Hexafluorobenzene (0.25 mL) was added and the mixture was heated to 50° C. t-Butyl chlorodifluoroacetate (3.80 g, 20.4 mmol, 1.0 eq) was added over a 50 minute period and the resulting mixture was stirred at 50° C. for 21 hours. A reaction aliquot, withdrawn and assayed by $^{19}$F NMR spectroscopy as described above, afforded a 64% yield of the title compound.

EXAMPLE 6

Isobutyl trimethylsilyl 2,2-difluoroketene acetal

To a mixture of 1.46 g (22.3 mg-atom, 1.1 eq) of zinc dust and 7.5 mL of 1,3-dimethylimidazolidin-2-one, stirred at 23° C. under dry nitrogen, was added 3.1 mL (2.7 g, 24 mmol, 1.2 eq) of chlorotrimethylsilane. The mixture was stirred at room temperature for 30 minutes. Hexafluorobenzene (0.25 mL) was added and the mixture was heated to 40° C. Isobutyl chlorodifluoroacetate (3.77 g, 20.2 mmol, 1.0 eq) was added over a 30 minute period and the resulting mixture was stirred at 40° C. for 15 hours. A reaction aliquot, withdrawn and assayed by $^{19}$F NMR spectroscopy as described above, afforded a 55% yield of the title compound.

EXAMPLE 7

($\beta$R, 4R)-$\alpha$,$\alpha$-Difluoro-2,2-dimethyl-$\beta$-[(trimethylsilyl)-oxy]-1,3-dioxolane-4-propanoic acid methyl ester The reaction mixture of Example 1 was heated to 40° C. for a total of 2 hours and then cooled to 0°–5° C. To this was added 5.61 mL (5.83 g, 36.9 mmol) of freshly distilled (R)-2,2-diethyl-1,3-dioxolane-4-carboxaldehyde. The cooling bath was removed and the mixture exothermed to a maximum of 29° C. over a 1 hour period. The mixture was stirred at ambient temperature for an additional 16.5 hours. A reaction aliquot, as assayed by $^{19}$F NMR spectroscopy (Example 1), afforded a 50% yield (based on the aldehyde) of the title compound as a 90:10 mixture of erythro and threo diastereomers, respectively.

The reaction mixture was poured into 45 mL of 1N aqueous NaHSO$_4$ and 50 g of crushed ice, and extracted with three 90-mL portions of ethyl acetate. The organic extracts were combined and washed with 100 mL of 1N pH 7 phosphate buffer. The aqueous phase was back-extracted with two 90-mL portions of ethyl acetate. The ethyl acetate phases were combined, dried (MgSO$_4$), and evaporated in vacuo. Capillary gas chromatographic analysis of the residue confirmed the yield obtained by $^{19}$F NMR integration.

EXAMPLE 8

($\beta$R, 4R)-$\alpha$,$\alpha$-Difluoro-2,2-dimethyl-$\beta$-[(trimethylsilyl)-oxy]-1,3-dioxolane-4-propanoic acid methyl ester The reaction mixture of Example 1 was heated to 40° C. for a total of 2 hours, and then cooled 0°–5° C. To this was added 2.74 mL (2.89 g, 22.2 mmol) of freshly distilled (R)-2,2-dimethyl-1,3-dioxolane-4-carboxaldehyde. The cooling bath was removed and the mixture exothermed to a maximum of 31° C. over a 1 hour period. The mixture was stirred at ambient temperature for an additional 16.5 hours. A reaction aliquot, as assayed by $^{19}$F NMR spectroscopy (Example 1), afforded an 83% yield (based on the aldehyde) of the title compound as a 89:11 mixture of erythro and threo diastereomers, respectively.

The product was isolated by the procedure described in Example 7. Capillary gas chromatographic analysis of the ethyl acetate extracts confirmed the yield obtained by $^{19}$F NMR integration.

EXAMPLE 9

($\beta$R, 4R)-$\alpha$,$\alpha$-Difluoro-2,2-dimethyl-$\beta$[(trimethyl-silyl)-oxy]-1,3-dioxolane-4-propanoic acid methyl ester To a mixture of 2.9 g (44 mg-atom, 1.1 eq) of zinc dust and 15 mL of 1,3-dimethyl-3,4,5,6-tetrahydro-2(1H)-pyrimidone (DMPU), stirred at 25° C. under dry nitrogen, was added 6.2 mL (5.3 g, 48 mmol, 1.2 eq) of chlorotrimethylsilane. The mixture was stirred at 25° C. for 30 minutes, and then cooled to 0°–5° C. Methyl chlorodifluoroacetate (4.40 mL, 5.87 g, 40.6 mmol, 1.0 eq) was added, the cooling bath was removed, and the mixture was allowed to exotherm to 38° C. over a 30 minute period. After an additional 30 minutes, the exotherm having subsided, the mixture was heated to 39°–41° C. for 2 hours. The mixture was cooled to 0° C. and 4.56 mL (4.81 g, 36.9 mmol, 0.91 eq) of freshly distilled (R)-2,2-dimethyl-1,3-dioxolane-4-carboxaldehyde was added. The mixture was allowed to warm slowly to 23° C. and after 24 hours the title compound was isolated by the procedure described in Example 7. Capillary gas chromatographic analysis of the ethyl acetate extracts afforded a 40% yield (based on the aldehyde) of the title compound as a 88:12 mixture of erythro and threo diastereomers, respectively.

EXAMPLE 10

($\beta$R, 4R)-$\alpha$,$\alpha$-Difluoro-2,2-dimethyl-$\beta$[(trimethyl-silyl)-oxy]-1,3-dioxolane-4-propanoic acid methyl ester To a mixture of 2.9 g (44 mg-atom, 1.1 eq) of zinc dust and 15 mL of 1,1,3,3-tetramethylurea, stirred at 25° C. under dry nitrogen, was added 6.2 mL (5.3 g, 48 mmol, 1.2 eq) of chlorotrimethylsilane. The mixture was stirred at 25° C. for 50 minutes, and then cooled to 0°–5° C. Methyl chlorodifluoroacetate (4.40 mL, 5.87 g, 40.6 mmol, 1.0 eq) was added, the cooling bath was removed, and the mixture was allowed to exotherm to 36° C. over a 30 minute period. After an additional 30 minutes, the exotherm having subsided, the mixture was heated to 39°–41° C. for 2 hours. The mixture was cooled to 7° C. and 4.56 mL (4.81 g, 36.9 mmol, 0.91 eq) of freshly distilled (R)-2,2-dimethyl-1,3-dioxolane-4-carboxaldehyde was added. The reaction mixture was allowed to exotherm to 38° C. After stirring for 14 hours, the title compound was isolated by the procedure described in Example 7. Capillary gas chromatographic analysis of the ethyl acetate extracts afforded a 58 % yield (based on the aldehyde) of the title compound as a 91:9 mixture of erythro and threo diastereomers, respectively.

COMPARATIVE EXAMPLES

The following comparative examples illustrate that when the present process is carried out with only conventional solvents such as acetonitrile, N,N-dimethylformamide, tetrahydrofuran and 1-methyl-2-pyrrolidinone, synthetically useful amounts of 2,2-difluoroketene silyl acetals are not produced.

EXAMPLE 11 (Comparative)

Methyl trimethylsilyl 2,2-difluoroketene acetal

To a suspension of 2.9 g (44 mg-atom, 1.1 eq) of zinc dust in 15 mL of acetonitrile, stirred at 23° C. under dry nitrogen, was added 6.2 mL (5.3 g, 49 mmol, 1.2 eq) of chlorotrimethylsilane. The resulting mixture was stirred at 23°–26° C. for 50 minutes and then cooled to 0°–5° C. Methyl chlorodifluoroacetate (4.4 mL, 40.6 mmol, 1.0 eq) and hexafluorobenzene (0.50 mL), a reaction calibration standard, were added and the reaction mixture was heated to 40° C. Reaction aliquots (0.30 mL) were withdrawn at the indicated times and assayed by $^{19}$F NMR spectroscopy to afford the following yields of the title compound:

| Aliquot | Elapsed Time (Hrs.) | % Yield |
|---|---|---|
| 1 | 1.75 | 0.8 |
| 2 | 3.25 | 1.2 |

After heating at 40° C. for 4 hours, the reaction mixture was refluxed for an additional 16.5 hours. Analysis of an aliquot of the resulting mixture by $^{19}$F NMR spectroscopy (vide supra) gave a 1.3% yield of the title compound and 88% recovery of methyl chlorodifluoroacetate.

EXAMPLE 12 (Comparative)

Methyl trimethylsilyl 2,2-difluoroketene acetal

To a mixture of 2.9 g (44 mg-atom, 1.1 eq) of zinc dust and N,N-dimethylformamide (15 mL), stirred at 24° C. under dry nitrogen, was added 290 μL (240 mg, 2.2 mmol, 0.05 eq) of chlorotrimethylsilane. The mixture was stirred at 25° C. for 30 minutes, and then cooled to 0° C. Methyl chlorodifluoroacetate (4.40 mL, 5.87 g, 40.6 mmol, 1.0 eq) was added followed by the slow dropwise addition, at 0°–5° C., of chlorotrimethylsilane (7.89 mL, 6.75 g; 60.9 mmol; 1.5 equiv). The mixture was stirred at 0°–5° C. for 1.5 hours and at 22°–32° C. for 65 minutes. The resulting mixture was assayed for the presence of the title compound by adding 4.56 mL (4.81 g, 36.9 mmol) of freshly distilled (R)-2,2-dimethyl-1,3-dioxolane-4-carboxaldehyde as described in Example 8, and measuring the amount of (βR,4R)-α,α-difluoro-2,2-dimethyl-β[(trimethylsilyl)-oxy]-1,3-dioxolane-4-propanoic acid methyl ester condensation product formed. None of the title compound could be detected.

EXAMPLE 13 (Comparative)

Methyl trimethylsilyl 2,2-difluoroketene acetal

To a mixture of 2.9 g (44 mg-atom, 1.1 eq) of zinc dust and tetrahydrofuran (15 mL), stirred at 23° C. under dry nitrogen, was added 6.2 mL (5.3 g, 48 mmol, 1.2 eq) of chlorotrimethylsilane. The mixture was stirred at 25° C. for 45 minutes, and then cooled to 0°–5° C. Hexafluorobenzene (0.500 mL), a reaction calibration standard, and methyl chlorodifluoroacetate (4.40 mL, 5.87 g, 40.6 mmol, 1.0 eq) were added, the cooling bath was removed, and the mixture was allowed to warm to 25° C. over a 1 hour period. The mixture was then heated to 40°–42° C. Reaction aliquots were withdrawn 1.5 and 3.0 hours after heating and were assayed by $^{19}$F NMR spectroscopy as described in Example 1. These aliquots were found to contain none of the title compound. The reaction mixture was then refluxed for 17 hours. A reaction aliquot withdrawn and assayed by $^{19}$F NMR spectroscopy as described above contained none of the title compound.

EXAMPLE 14 (Comparative)

Methyl trimethylsilyl 2,2-difluoroketene acetal

To a mixture of 2.9 g (44 mg-atom, 1.1 eq) of zinc dust and 15 mL of 1-methyl-2-pyrrolidinone, stirred at 25° C. under dry nitrogen, was added 6.2 mL (5.3 g, 48 mmol, 1.2 eq) of chlorotrimethylsilane. The mixture exothermed sharply to 37° C., at which time an ice-bath was applied to cool the mixture to 30° C. After the exotherm subsided, the mixture was cooled to 0°–5° C. Hexafluorobenzene (0.500 mL), a reaction calibration standard, and methyl chlorodifluoroacetate (4.40 mL, 5.87 g, 40.6 mmol, 1.0 eq) were added and the mixture was allowed to exotherm to 41° C. over a 45 minute period. An ice-bath was applied to maintain the reaction temperature between 30°–33° C. After the exotherm subsided (30 minutes) the mixture was heated to 40° C. Reaction aliquots were withdrawn at the indicated times after heating and assayed by $^{19}$F NMR spectroscopy as described in Example 1. The percent yield of title compound and percent recovery of chloro ester in each aliquot are indicated below:

| Aliquot | Elapsed Time (Hrs.) | % Yield | % Recovery |
|---|---|---|---|
| 1 | 2.0 | 6 | 44 |
| 2 | 3.5 | 4 | 35 |
| 3 | 25.0 | 0 | 6 |

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A process for preparing a 2,2-difluoroketene silyl acetal of the formula

(I)

wherein $R^1$, $R^2$, $R^3$, and $R^4$ are each independently selected from alkyl and aryl groups or substituted alkyl or substituted aryl groups; comprising contacting a chlorodifluoroacetate of the formula

(II)

wherein $R^4$ is as defined above; with a halosilane of the formula

$$XSiR^1R^2R^3 \qquad (III);$$

wherein X is chloro or bromo, and $R^1$, $R^2$, and $R^3$ are as defined above; in a solvent selected from the group consisting of cyclic and acyclic tetraalkyl ureas or mixtures thereof; in the presence of a reducing agent.

2. The process of claim 1 wherein the halosilane is selected from the group consisting of chloro- or bromo--trimethylsilane, -triethylsilane, -isopropyldimethylsilane, -t-butyldimethylsilane, -(triphenylmethyl)dimethylsilane, -t-butyldiphenylsilane, -methyldiisopropylsilane, -methyldi-t-butylsilane, -tribenzylsilane, -tri-p-xylylsilane, -triisopropylsilane, and -triphenylsilane.

3. The process of claim 1 in which a co-solvent is used, with said co-solvent being selected from the group consisting of acetonitrile, tetrahydrofuran, and 1,2-dimethoxyethane, or mixtures thereof.

4. The process of claim 1 wherein the solvent is selected from the group consisting of 1,3,4,5-tetramethyl-2-imidazolidinone; 1,3,4,4-tetramethyl-2-imidazolidinone; 1,3,4,4,5,5-hexamethylimidazolidinone; 1,3,4,6-tetramethyl-3,4,5,6-tetrahydro-2(1H)-pyrimidinone; 1,3,4-trimethyl-3,4,5,6-tetrahydro-2(1H)-pyrimidinone; 1,3,5-trimethyl-3,4,5,6-tetrahydro-2(1H)-pyrimidinone; 1,3-diisopropyl-1,3-dimethyl urea; 3-ethyl-1,3-dimethyl-1-isopropyl urea; 1,3,5,5-tetramethyl-3,4,5,6-tetrahydro-2(1H)-pyrimidinone; 1,3-dimethyl-3,4,5,6-tetrahydro-2(1H)-pyrimidinone (DMPU); 1,3-dimethyl-2-imidazolidinone (DMI); 1,1,3,3-tetramethyl urea (TMU); 1,1,3,3-tetraethyl urea; 1,1,3-triethyl-3-methyl urea; 1,3,4,4-tetramethyl-tetrahydro-pyrimidin-2-one; 1-ethyl-1,3,3-trimethyl urea; 1-isopropyl-1,3,3-trimethyl urea; hexahydro-1,3-dimethyl-2H-1,3-diazepin-2-one; 1-ethyl-3-methyl-imidazolidin-2-one; 1-tert-butyl-1,3,3-trimethyl urea; 1,3-diethyl-1,3-dimethyl urea; di-(pyrrolidin-1-yl)-methanone; 1,3-diethyl-imidazolidin-2-one; 1,3,4-trimethyl-imidazolidin-2-one; 1,1-diethyl-3,3-dimethyl urea; 1,3-diethyl-3,4,5,6-tetrahydro-pyrimidin-2-one; and 1,3,4,4,5-pentamethyl-2-imidazolidinone; and mixtures thereof.

5. The process of claim 1 wherein the solvent is 1,3-dimethylimidazolidin-2-one.

6. The process of claim 1 wherein the reducing agent is zinc.

7. A process for preparing a $\alpha,\alpha$-difluoro-$\beta$-silyloxy-1,3-dioxolane-4-propanoic acid ester of the formula

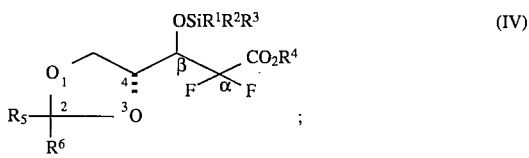
(IV)

wherein $R^1$, $R^2$, $R^3$, and $R^4$ are each independently selected from alkyl and aryl groups or substituted alkyl or substituted aryl groups and $R^5$ and $R^6$ are independently selected from hydrogen and $C_1$–$C_3$ alkyl groups or together form part of a carbocyclic ring in which they comprise a —$(CH_2)_n$— moiety where n is an integer from 3 to 6; comprising contacting a 2,2-difluoroketene silyl acetal of the formula

(I)

wherein $R^1$, $R^2$, $R^3$, and $R^4$ are each independently selected from alkyl and aryl groups or substituted alkyl or substituted aryl groups prepared by contacting a chlorodifluoroacetate of the formula

(II)

wherein $R^4$ is as defined above; with a halosilane of the formula

(III);

wherein X is chloro or bromo, and $R^1$, $R^2$, and $R^3$ are as defined above; in a solvent selected from the group consisting of cyclic and acyclic tetraalkyl ureas, mixtures thereof, or a mixture consisting of the solvent and a co-solvent which is either acetonitrile or tetrahydrofuran or mixtures thereof; in the presence of a reducing agent; with a glyceraldehyde derivative of the formula

(V)

wherein $R^5$ and $R^6$ are as defined above.

8. The process of claim 7 wherein the glyceraldehyde derivative is of the formula

(Va)

9. The process of claim 7 wherein the glyceraldehyde derivative is of the formula

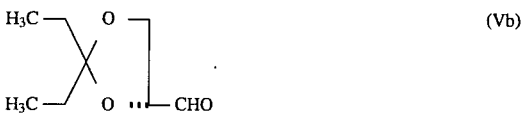
(Vb)

10. The process of claim 7 wherein the halosilane is selected from the group consisting of chloro- or bromo- -trimethylsilane, -triethylsilane, -isopropyldimethylsilane, -t-butyldimethylsilane, -(triphenylmethyl)dimethylsilane, -t-butyldiphenylsilane, -methyldiisopropylsilane, -methyldi -t-butylsilane, -tribenzylsilane, -tri-p-xylylsilane, -triisopropylsilane, and -triphenylsilane.

11. The process of claim 7 wherein the solvent is selected from the group consisting of 1,3,4,5-tetramethyl-2-imidazolidinone; 1,3,4,4-tetramethyl-2-imidazolidinone; 1,3,4,4,5,5-hexamethylimidazolidinone; 1,3,4,6-tetramethyl-3,4,5,6-tetrahydro-2(1H)-pyrimidinone; 1,3,4-trimethyl-3,4,5,6-tetrahydro-2(1H)-pyrimidinone; 1,3,5-trimethyl-3,4,5,6-tetrahydro-2(1H)-pyrimidinone; 1,3-diisopropyl-1,3-dimethyl urea; 3-ethyl-1,3-dimethyl-1-isopropyl urea; 1,3,5,5-tetramethyl-3,4,5,6-tetrahydro-2(1H)-pyrimidinone; 1,3-dimethyl-3,4,5,6-tetrahydro-2(1H)-pyrimidinone (DMPU); 1,3-dimethyl-2-imidazolidinone (DMI); 1,1,3,3-tetramethyl urea (TMU); 1,1,3,3-tetraethyl urea; 1,1,3-triethyl-3-methyl urea; 1,3,4,4-tetramethyl-tetrahydro-pyrimidin-2-one; 1-ethyl-1,3,3-trimethyl urea; 1-isopropyl-1,3,3-trimethyl urea; hexahydro-1,3-dimethyl-2H-1,3-diazepin-2-one; 1-ethyl-3-methyl-imidazolidin-2-one; 1-tert-butyl-1,3,3-trimethyl urea; 1,3-diethyl-1,3-dimethyl urea; di-(pyrrolidin-1-yl)-methanone; 1,3-diethyl-imidazolidin-2-one; 1,3,4-trimethyl-imidazolidin-2-one; 1,1-diethyl-3,3-dimethyl urea; 1,3-diethyl-3,4,5,6-tetrahydro-pyrimidin-2-one; and 1,3,4,4,5-pentamethyl-2-imidazolidinone; and mixtures thereof.

12. The process of claim 11 wherein the solvent is 1,3-dimethylimidazolidin-2-one.

13. The process of claim 7 wherein the reducing agent is zinc.

* * * * *